United States Patent [19]

Milosevic et al.

[11] Patent Number: 5,308,983
[45] Date of Patent: May 3, 1994

[54] SPECTROSCOPIC ACCESSORY WITH MICROSCOPE ILLUMINATOR

[75] Inventors: Milan Milosevic, Fishkill; Nicolas J. Harrick, Ossining; Craig R. Wisch, Croton on Hudson, all of N.Y.

[73] Assignee: Harrick Scientific Corporation, Ossining, N.Y.

[21] Appl. No.: 907,629

[22] Filed: Jul. 2, 1992

[51] Int. Cl.⁵ .................... G01N 21/17; G01N 21/01
[52] U.S. Cl. .................. 250/339.01; 250/341; 356/244; 359/368; 359/798
[58] Field of Search ............ 250/339, 341, 358.1; 356/244; 359/798, 800, 656, 657, 658, 659, 660, 661, 662, 368, 391

[56] References Cited

U.S. PATENT DOCUMENTS

| | | | |
|---|---|---|---|
| 1,954,755 | 4/1934 | Heine | 359/661 |
| 4,664,486 | 5/1987 | Landre et al. | 359/661 X |
| 5,093,580 | 3/1992 | Sting | 356/455 X |
| 5,126,244 | 6/1993 | Esaki et al. | 356/244 X |

Primary Examiner—Constantine Hannaher
Assistant Examiner—Edward J. Glick

[57] ABSTRACT

An optical accessory for reflection spectroscopy having a very small sampling area and provided with a microscope for aiding the user to locate a sample to be analyzed on the active sampling area where it can interact with a radiation beam. The microscope is characterized by fiber optic bundles to supply sample illumination via a cone-shaped light-funnelling tip terminated in a thin hard optically transparent wear tip, e.g., of sapphire. The microscope is also used to apply pressure via the wear tip to the sample while it is being illuminated and while it can be viewed to maximize interaction with the radiation.

31 Claims, 4 Drawing Sheets

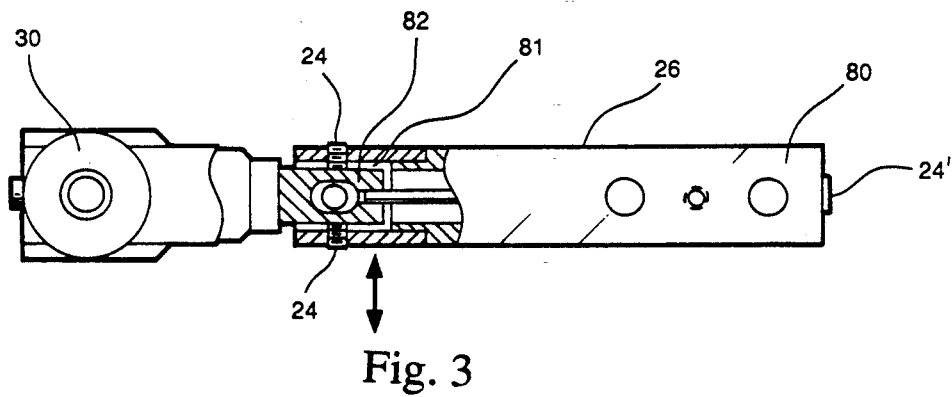
Fig. 3
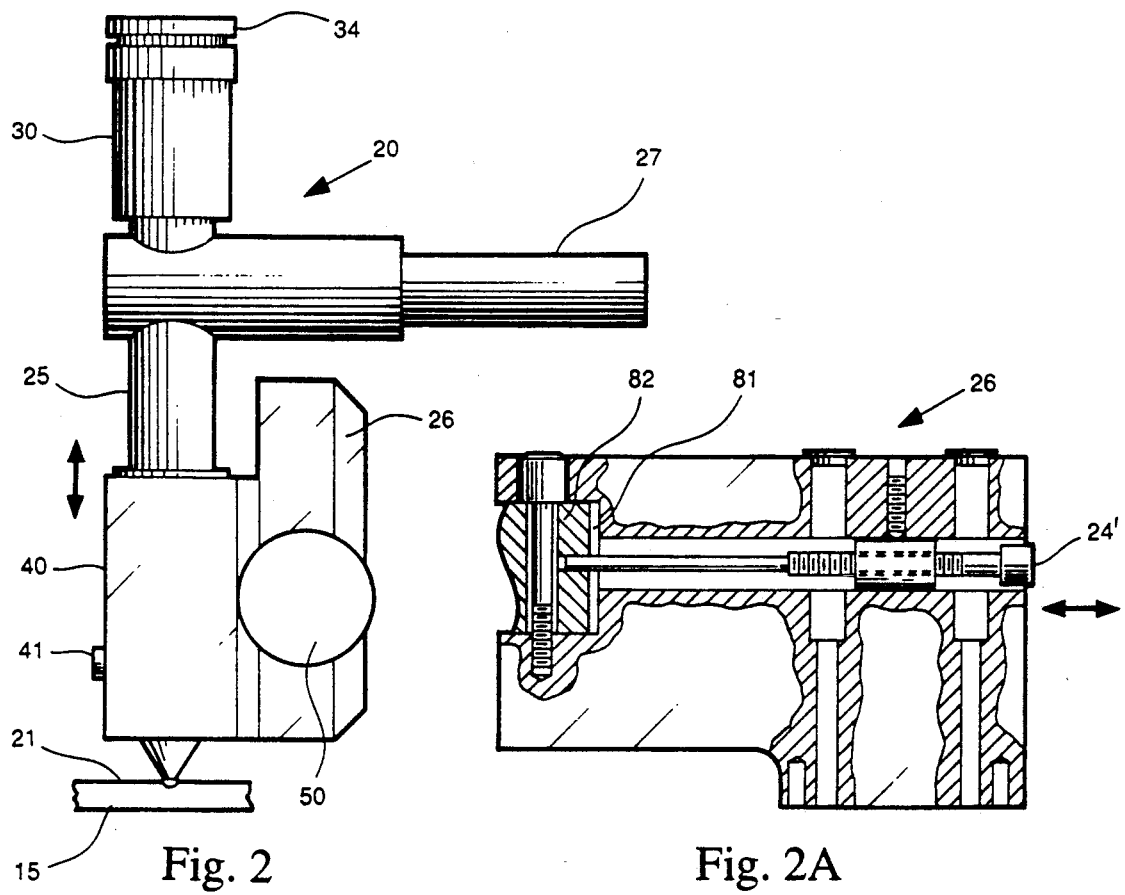
Fig. 2
Fig. 2A

SPECTROSCOPIC ACCESSORY WITH MICROSCOPE ILLUMINATOR

RELATED CASE

Commonly-owned, copending U.S. application, Ser. No. 762,577, filed Sep. 19, 1991, entitled "Ultra-Small Sample Analyzer For Internal Reflection Spectroscopy" now U.S. Pat. No. 5,210,418.

BACKGROUND OF THE INVENTION

This invention relates to spectroscopic accessories for analysis of samples by various reflectance techniques, and in particular to such accessories equipped with a microscope.

The referenced copending application describes an optical accessory for analysis of samples by internal reflection spectroscopy, the contents of which are hereby incorporated by reference. A feature of the accessories in that case is a small sampling surface located at the flat top of a hard hemisphere. The analyzing radiation—which for this accessory is in the spectral range from near to far infrared—enters the curved hemisphere surface and is focussed to a very small active area, typically 1 mm or less in size, at the top of the sampling surface. This irradiated area, referred to as the active sampling area, is often referred to as the "hot spot". A sample pressed down hard on the top sampling surface over the hot spot will interact with the radiation as is well known in internal reflection spectroscopy (IRS), modulate the radiation, which internally reflects from the sampling surface, exits the hemisphere, and ultimately is directed to the spectrometer for detection and processing into the usual spectra. A feature of this accessory is that small samples and small areas of large samples can be analyzed under high pressure with good signal-to-noise ratios providing excellent spectra despite the relatively low interaction level. However, a problem that can arise is that the precise area of the sample to be analyzed may not be located over the hot spot because of its small size.

SUMMARY OF THE INVENTION

An object of the invention is a spectroscopic accessory providing means allowing the user to view the sample with relation to the active part of the sampling surface to ensure its proper location.

Another object of the invention is a spectroscopic accessory simplifying the proper location of a sample to be analyzed.

A further object of the invention is a novel microscope for use with optical accessories.

In accordance with one aspect of the invention, the spectroscopic accessories are provided with a microscope positioned such that a user can view a magnified image of the active sampling surface area, thereby enabling the user to accurately position the sample area desired to be analyzed.

In accordance with another aspect of the invention, the spectroscopic accessories are provided with means for applying pressure to press a sample against the active sampling surface area. The pressure applying means employs an optically transparent, hard, wear tip. A combined microscope-illuminator integrated with the pressure applying means is configured such that the illuminating rays and the microscope optical paths pass through the optically transparent wear tip. Hence, the tip, which becomes illuminated, becomes the means to apply the pressure to the sample while under magnified observation by the user thereby guaranteeing proper alignment of the desired sampling area with the active sampling area or hot spot. In a preferred embodiment, the illuminator uses optical fibers to carry the illuminating rays to the wear tip.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

BRIEF DESCRIPTION OF THE DRAWINGS

In the drawings:

FIG. 2 is a side view of the microscope incorporated in the FIG. 1 accessory;

FIG. 2A is a cross-sectional view of a part of the microscope shown in FIG. 2;

FIG. 3 is a top view of the microscope of FIG. 2;

DETAILED DESCRIPTION OF THE PREFERRED EMBODIMENTS

Figure 1:
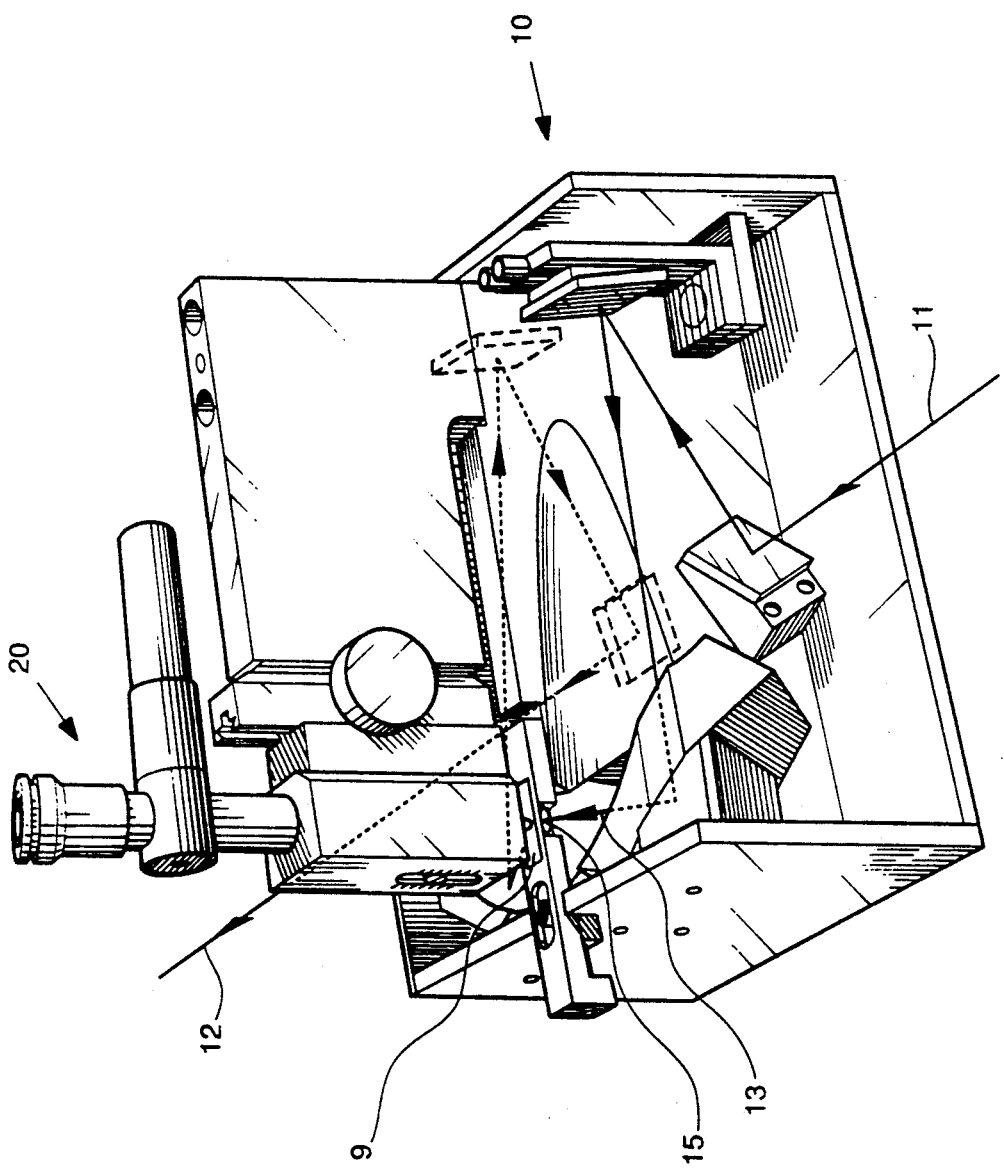
FIG. 1 is a side perspective view of the optical accessory described in the referenced patent application, Ser. No. 762,577, equipped with one form of a microscope according to the invention.

FIG. 1 shows the accessory of the copending application, with one side and the top removed to show the interior. The accessory 10 usually sits in the sampling compartment of a conventional spectrometer, which supplies an analyzing beam of radiation 11, e.g., in the IR, UV or visible range, and which then detects the exiting radiation 12 for processing into conventional spectra. After redirection via several mirrors and reflectors, the beam at 13 enters the curved hemispherical surface of a hemisphere 15 which functions as the internal reflection element (IRE) for internal reflectance spectroscopy (IRS). A typical diameter of the hemisphere is about 3 mm. The top is flat and exposed, and acts as the sampling surface for receiving a sample 9 to be analyzed. The optical geometry is such that the active sampling area or hot spot is about 0.25 mm or less in size. Unless the sample is located properly on the hot spot, it cannot be analyzed by the beam which internally reflects from the flat top of the crystal. The function of the microscope 20 is to enable the user to accurately locate the desired area of the sample to be analyzed at the hot spot.

FIG. 2 shows the microscope 20. Part of the hemisphere 15 on the accessory 10 is shown at the bottom. The top sampling surface is designated 21.

Figure 4:
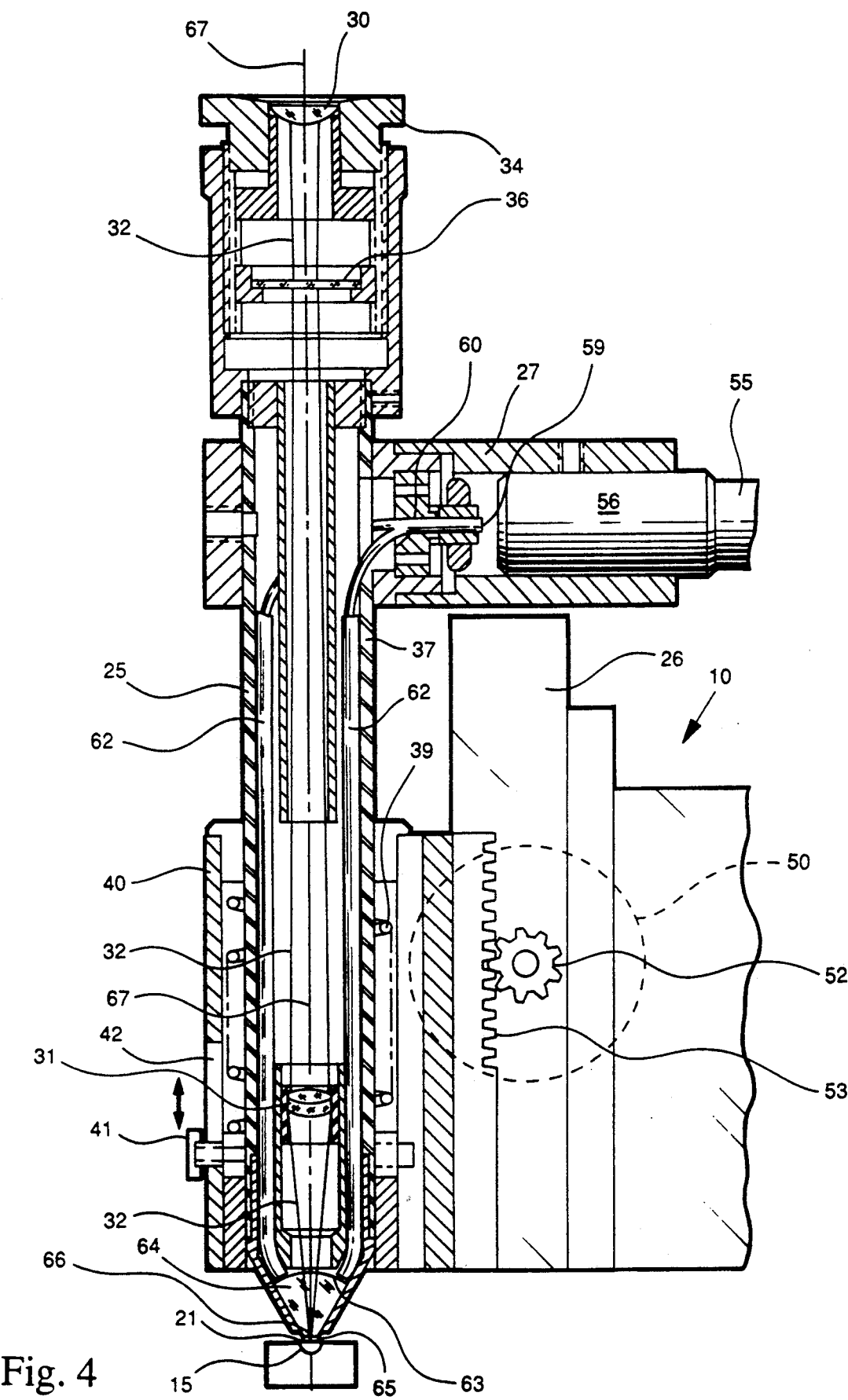
FIG. 4 is an enlarged cross-sectional view of the microscope of FIG. 2.
Figure 5:
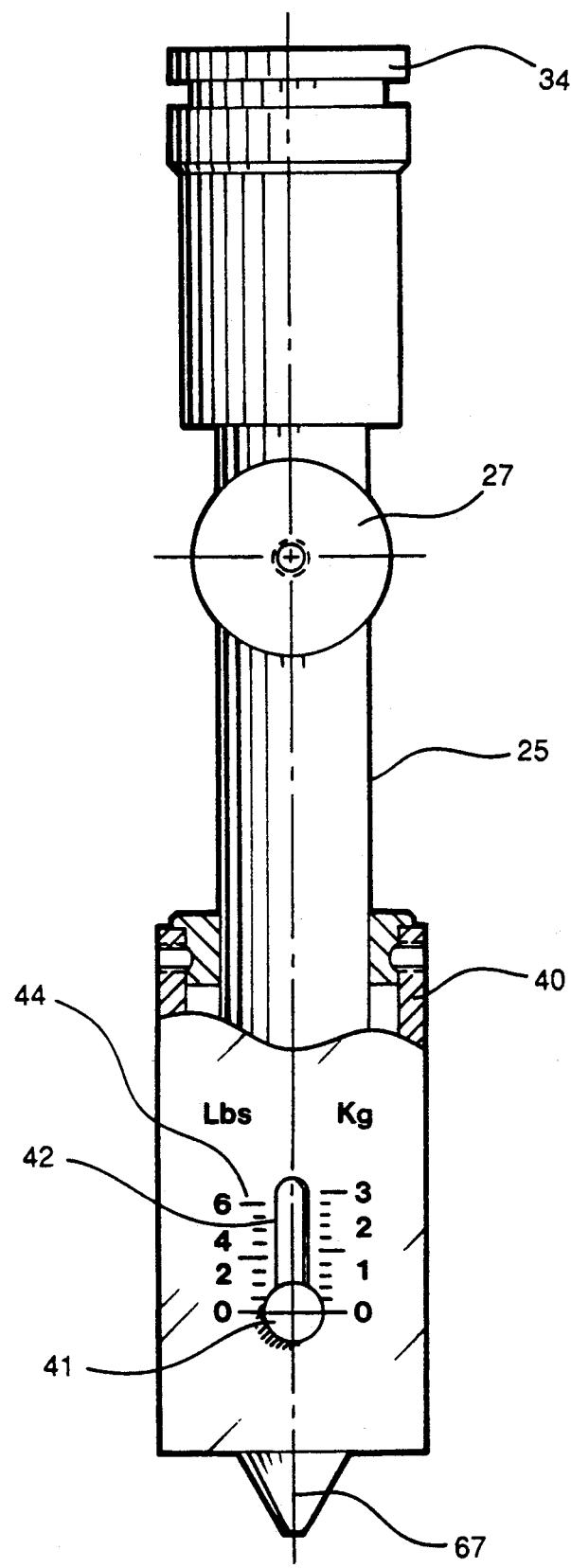
FIG. 5 is a front, partly cross-sectional view of the microscope of FIG. 2.

The microscope 20 comprises a vertical light tube 25, a lower adjustment part 26, and a horizontal illuminator 27. The light tube 25 comprises at the top the usual ocular 30, and at the bottom the usual objective 31. FIG. 4 shows the internal construction and some light paths 32. The ocular 30 is held in an eyepiece 34 that is vertically adjustable. A cross-line reticle 36 is provided at the top as an optical aid. The structure is supported by a stainless steel housing 37 which is mounted on the adjustment part 26, which in turn is supported on the accessory 10 as shown in FIG. 1.

At the bottom of the light tube 25 is a device for enabling pressure to be applied to a sample. The structure comprises an outer tube 40, fixed to the accessory housing, within which outer tube 40 the light tube 25 is allowed a limited amount of vertical movement against a compression spring 39. In the embodiment illustrated, which is not meant to be limiting, the vertical movement allowed will provide a pressure on the sample of up to six lbs. A projection 41, movable vertically within a slot 42 in the outer tube 40, serves as the pressure indicator. As the spring 39 is compressed, the pressure of the light tube 25 on the sampling surface increases. A scale 44 informs the user of the amount of the pressure, recorded in lbs or kg. The spring 39 is biased to push the microscope toward its lowermost or zero pressure position.

The functions of the adjustment part 26 include to adjust the objective position for focussing purposes, and to allow the user to move the microscope laterally (horizontally)—also in and out (left and right in the side view)—about 1-2 mm with respect to the sampling area for alignment purposes. FIGS. 2A and 3 show the internal structure. An arm 80 supports the microscope 20 on the accessory 10 via a slot 81 which accommodates a mating part 82 capable of small movements within the slot 81. Set screws 24 will move the entire microscope 20 relative to the part 26 about 1-2 mm laterally, vertically in FIG. 3. Cap screw 24' is connected as a lead screw to part 82 to move the entire microscope 20 relative to the part 26 about +/−1 mm laterally, horizontally in FIG. 2A.

A third important function of the adjustment part 26 is to move the microscope vertically from a position above the sampling surface down to a position where it can contact the sample. This vertical movement is obtained using the knob 50. The knob 50 is connected to a small pinion 52 which engages a rack 53 to provide the desired vertical movement.

The illumination for the microscope is supplied by the illuminator 27, which can accommodate a battery 55 powering a light source 56, such as a small bulb. Alternatively, the light source can be powered from an external source. The rays from the source 56 illuminate the ends 59 of a fiber optics bundle 60. The bundle 60 separates into four separate sub-bundles 62 which evenly circumferentially surround the microscope light paths 32. While four sub-bundles 62 are preferred, two to six sub-bundles will perform satisfactorily. Two of the sub-bundles 62 only are shown in FIG. 4. The sub-bundles 62 extend vertically downward and terminate adjacent the top of a generally cone-shaped, optically transparent, glass or plastic piece 64 having a hemispherical top 63. The latter acts to funnel or concentrate the rays to its tip 66. The diameter of the cone top 63 is about 5-15 mm. A preferred value is 10 mm. At the narrow end or tip 66 of the cone-shaped piece 64 is bonded by transparent optical cement a hard, optically transparent, thin, wear piece 65, for example, of sapphire. Sapphire is preferred because it has good optical transparency and it will wear well. The diameter of the wear tip 65 is about 0.5-1.5 mm, with 1.0 mm preferred. Thus, the illuminating rays pass along the optical fibers 60, 62, through the cone-shaped piece 64, through the wear tip 65 directly onto the sampling surface 21 or sample placed thereon concentrated at the vertical axis 67 of the microscope which is also its optical axis.

The optical system is focussed on the wear surface at the bottom of the wear tip 65. The knob 50 when rotated brings the wear surface into contact with the sample. If the sample is not in focus, the user can still adjust the focus using the eyepiece 34 on top.

In operation, a sample 9 is placed on the sampling surface 21. The light tube 25 is lowered by operating the knob 50 until the sapphire wear tip 65 is in contact with the sample. The desired focussing is achieved automatically. With the illuminator on, the sample is brightly illuminated. Any further rotation of the knob 50 will increase or decrease the pressure on the sample. This adjustment does not affect the focussing of the microscope. With the system properly adjusted, the optical axis 67 is centered on the hot spot. The reticle 36 aids the user in locating the precise sample area desired. The total lens power is about 50, so that the user sees a 50× magnified image of the sample.

An important benefit of the construction of the invention is not only that the sample at the hot spot can be brightly illuminated, but also that it allows the user to view the sample through the optically transparent wear tip 65 while pressure is applied and while it can be varied via the knob 50. Hence, the user can be certain that the sample remains over the hot spot when the desired pressure is applied. It should be recognized that in IRS, the interaction is between the sample surface and the evanescent wave emanating from the internally reflected beam. The height of that wave is very small, of the order of 1 micron for IR radiation. Unless the sample surface is within that range, no interaction is possible. The function of the pressure is to ensure a good contact to maximize the interaction. Note also that the accessory can be used with thin film samples, so pressure is necessary for good contact. Also, the accessory can be used for analyzing panel surfaces, which may be curved or irregular, so again pressure is needed to ensure good contact.

Figure 6:
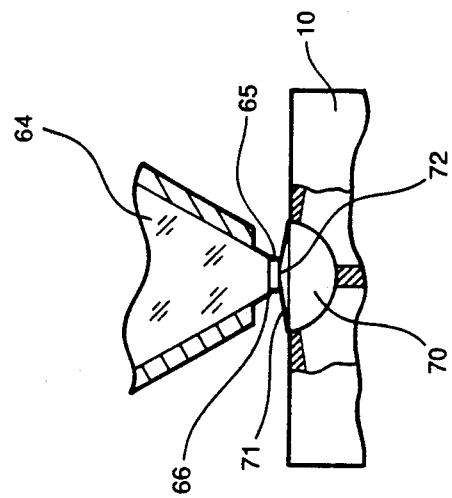
FIG. 6 is a sideview of an internal reflection element with a modified sampling surface for the accessory.

Since the provision of the microscope greatly simplifies the task of aligning the sample to the active sampling area, it becomes possible to reduce even further the diameter of the sampling surface. In the referenced copending application, the hemisphere 15, preferably of silicon, had a flat top that was equal to the hemisphere diameter. FIG. 6 shows a modification in which the hemisphere 70 has been circumferentially bevelled at 71, with a slope of about 5°-10° so that now the new sampling surface reduced to about 0.3 mm in diameter for a hemisphere 70 of the same diameter as before of 3 mm. As a result, even smaller sample areas can be investigated than was possible before with this accessory. The cone-shaped piece 64, preferably of Lucite, has the sapphire wear tip 65 bonded to it, so that it fully covers the new sampling surface.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A spectroscopic accessory for sample analysis comprising:
   (a) sample supporting means having an active sampling area, (b) means for directing an analyzing radiation beam to the active sampling area, (c) means for redirecting the analyzing radiation beam after interaction with a sample on the active sampling area, (d) means including an optically-transparent element for applying pressure for pressing a desired area of the sample against the active sampling area, (e) means for viewing under magnification through the optically-transparent element the desired area of the sample while the pressure is applied.

2. A spectroscopic accessory for sample analysis comprising:

(a) sample supporting means having an active sampling area on the order of 1 mm and smaller than the area of the sample supporting means, (b) means for directing an analyzing radiation beam to the active sampling area, (c) means for redirecting the analyzing radiation beam after interaction with a sample on the active sampling area, (d) means for applying pressure for pressing a desired area of the sample against the active sampling area, (e) means for viewing under magnification the desired area of the sample relative to the active sampling area while the analyzing radiation is interacting with the sample for accurately aligning the desired area of the sample to the active sampling area.

3. The spectroscopic accessory as claimed in claim 2, wherein the means for viewing comprises a microscope.

4. The spectroscopic accessory as claimed in claim 3, wherein the means for applying pressure is integrated with the means for viewing.

5. The spectroscopic accessory as claimed in claim 3, further comprising means for laterally moving the microscope a small distance relative to the active sampling area.

6. A microscope for use with an optical analyzing accessory, said microscope comprising a light tube having a bottom and having an optical path extending vertically to the bottom, said light tube having at its bottom an optically transparent wear tip in the optical path, said wear tip being hard relative to an object below it to be viewed and having a diameter of about 1.5 mm or less such that a magnified view of an object of 1.5 mm or less below the tip while the tip is in contact with the object is obtained.

7. The microscope as claimed in claim 6, further comprising means for illuminating the wear tip.

8. The microscope as claimed in claim 7, wherein the means for illuminating comprises plural spaced optical fibers.

9. The microscope as claimed in claim 8, wherein the plural optical fibers extend inside the light tube and surround the optical path.

10. The microscope as claimed in claim 9, wherein the means for illuminating includes a portion extending transverse to the light tube which houses a light source.

11. A spectroscopic accessory for sample analysis comprising:

(a) sample supporting means having an active sampling area, (b) means for directing an analyzing radiation beam to the active sampling area, (c) means for redirecting the analyzing radiation beam after interaction with a sample on the active sampling area, (d) means for applying pressure for pressing a desired area of the sample against the active sampling area, (e) means for viewing under magnification the desired area of the sample while the pressure is applied, (f) means for varying the applied pressure.

12. The spectroscopic accessory as claimed in claim 11, wherein the means for viewing allows viewing while the pressure is varied.

13. A spectroscopic accessory for sample analysis comprising:

(a) sample supporting means having an active sampling area, (b) means for directing an analyzing radiation beam to the active sampling area, (c) means for redirecting the analyzing radiation beam after interaction with a sample on the active sampling area, (d) means for applying pressure for pressing a desired area of the sample against the active sampling area, said means for applying pressure including optically transparent elements, (e) means for viewing under magnification the desired area of the sample while the pressure is applied.

14. The spectroscopic accessory as claimed in claim 13, wherein one of the optically transparent elements comprises an optically transparent wear piece.

15. A spectroscopic accessory for sample analysis comprising:

(a) sample supporting means having an active sampling area smaller than the area of the sample supporting means, (b) means for directing an analyzing radiation beam to the active sampling area, (c) means for redirecting the analyzing radiation beam after interaction with a sample on the active sampling area, (d) means for applying pressure for pressing a desired area of the sample against the active sampling area, (e) means for viewing under magnification the desired area of the sample relative to the active sampling area for accurately aligning the desired area of the sample to the active sampling area, (f) the active sampling area being horizontally oriented, (g) the means for viewing comprising a microscope having an optical path extending vertically above the active sampling area and being provided at the active sampling area with an optically transparent, small diameter wear tip in the optical path such that a magnified view of the sample below the tip while the tip is in contact with the sample is obtained.

16. The spectroscopic accessory as claimed in claim 15, further comprising means for varying the pressure applied to the sample while the sample is viewed.

17. The spectroscopic accessory as claimed in claim 16, wherein the wear tip comprise sapphire.

18. The spectroscopic accessory as claimed in claim 17, wherein the small diameter is in the range of 0.5–1.5 mm.

19. The spectroscopic accessory as claimed in claim 15, further comprising means for illuminating the wear tip.

20. The spectroscopic accessory as claimed in claim 19, wherein the means for illuminating comprises plural spaced optical fibers.

21. The spectroscopic accessory as claimed in claim 20, wherein the plural optical fibers extend inside the microscope and surround the optical path.

22. The spectroscopic accessory as claimed in claim 21, wherein the means for illuminating includes a portion extending transverse to the optical path which houses a light source.

23. A spectroscopic accessory for sample analysis comprising:
   (a) sample supporting means having an active sampling area smaller than the area of the sample supporting means, said sample supporting means comprising a hemisphere,
   (b) means for directing an analyzing radiation beam to the active sampling area,
   (c) means for redirecting the analyzing radiation beam after interaction with a sample on the active sampling area,
   (d) means for applying pressure for pressing a desired area of the sample against the active sampling area,
   (e) means for viewing under magnification the desired area of the sample relative to the active sampling area for accurately aligning the desired area of the sample to the active sampling area.

24. The spectroscopic accessory as claimed in claim 23, wherein the active sampling area is located on a top flat surface portion of the hemisphere.

25. The spectroscopic accessory as claimed in claim 24, wherein the top flat surface portion is surrounded by a bevelled region whereby the top flat surface portion has a smaller diameter than that of the hemisphere.

26. A microscope for use with an optical analyzing accessory, said microscope comprising a light tube having a bottom and having an optical path extending vertically above the bottom of the light tube, said light tube having at its bottom an optically transparent, small diameter wear tip in the optical path such that a magnified view of an object below the tip while the tip is in contact with the object is obtained, means for applying pressure via the wear tip on the object.

27. The microscope as claimed in claim 26, further comprising means for varying the pressure applied to the object while the object is viewed.

28. The microscope as claimed in claim 27, wherein the wear tip comprise sapphire.

29. The microscope as claimed in claim 28, wherein the small diameter is in the range of 0.5–1.5 mm.

30. The microscope as claimed in claim 27, wherein the light tube comprises at its bottom above the wear tip a cone-shaped optically transparent element for concentrating light onto the wear tip.

31. A microscope for use with an optical analyzing accessory, said microscope comprising a light tube having an optical path extending vertically above a bottom of the light tube, said light tube having at its bottom an optically transparent, small diameter wear tip in the optical path such that a magnified view of an object below the tip while the tip is in contact with the object is obtained, means for laterally moving the microscope a small distance relative to the object to be viewed.

* * * * *